United States Patent
Perlman

(10) Patent No.: US 7,485,608 B2
(45) Date of Patent: Feb. 3, 2009

(54) PH-BUFFERED ALKYLENE CARBONATE NAIL POLISH AND PAINT REMOVER

(76) Inventor: Daniel Perlman, 94 Oakland Ave., Arlington, MA (US) 02476

( * ) Notice: Subject to any disclaimer, the term of this patent is extended or adjusted under 35 U.S.C. 154(b) by 0 days.

(21) Appl. No.: 10/800,492

(22) Filed: Mar. 15, 2004

(65) Prior Publication Data

US 2005/0202982 A1  Sep. 15, 2005

(51) Int. Cl.
*A61K 7/50* (2006.01)

(52) U.S. Cl. .......... 510/118; 510/407; 510/505

(58) Field of Classification Search ............ None
See application file for complete search history.

(56) References Cited

U.S. PATENT DOCUMENTS

| | | | | |
|---|---|---|---|---|
| 4,508,634 A | * | 4/1985 | Elepano et al. ........ | 510/139 |
| 4,594,111 A | | 6/1986 | Coonan ................. | 134/3 |
| 4,801,331 A | | 1/1989 | Murase ................. | 106/3 |
| 5,007,969 A | | 4/1991 | Doscher ............... | 134/38 |
| 5,098,591 A | * | 3/1992 | Stevens ............... | 510/106 |
| 5,215,675 A | * | 6/1993 | Wilkins et al. ........ | 510/206 |
| 5,258,070 A | | 11/1993 | Monteleone et al. .... | 106/311 |
| 5,486,305 A | | 1/1996 | Faryniarz et al. ...... | 252/162 |
| 6,040,284 A | | 3/2000 | Marquis et al. ........ | 510/201 |
| 6,521,572 B2 | | 2/2003 | Perlman .............. | 510/118 |
| 6,586,380 B2 | | 7/2003 | Marquis et al. ........ | 510/201 |

* cited by examiner

*Primary Examiner*—Necholus Ogden, Jr.
(74) *Attorney, Agent, or Firm*—Ames IP Law; Wesley B Ames

(57) ABSTRACT

A composition with improved chemical stability and increased the efficacy as an alkylene carbonate-containing nail polish remover or general purpose solvent, such as a paint thinner or stripper is disclosed. The composition includes:

(i) between 10% and 98% by weight of at least one alkylene carbonate solvent, (ii) between 1.5% and 25% by weight water, and (iii) an effective amount of a pH-buffering agent that maintains the pH of the composition between approximately pH 2 and pH 6.5 and that is chemically inert in the composition. The water in the composition functions to increase the rate at which the composition dissolves, e.g., nail lacquers, and the pH-buffering agent functions to stabilize the alkylene carbonate solvent against hydrolytic decomposition from pH-altering contaminants that may be introduced into the composition.

23 Claims, No Drawings

PH-BUFFERED ALKYLENE CARBONATE NAIL POLISH AND PAINT REMOVER

CROSS REFERENCE TO RELATED APPLICATIONS

N/A

STATEMENT REGARDING FEDERALLY SPONSORED RESEARCH OR DEVELOPMENT

N/A

BACKGROUND OF THE INVENTION

This invention relates to the field of cosmetics and more specifically to nail polish remover products in which the chemical stability and efficacy of alkylene carbonate-containing products are improved and to such products that comply with new government regulations by utilizing low vapor pressure volatile organic compounds (LVP-VOCs). The invention relates, furthermore, to alkylene carbonate-containing general cleaners such as paint remover (or stripper) products with improved stability and efficacy.

For reasons of economy and efficacy, the most common solvent systems utilized for removing nail polishes (also known as nail lacquers) have been acetone and ethyl acetate. However, many problems including skin irritation and skin and cuticle desiccation are associated with the use of these solvents at high concentrations, and many remedies have been described for these problems (See, Curtis (U.S. Pat. No. 4,485,037), Hofmann (U.S. Pat. No. 4,824,662), Hofmann (U.S. Pat. No. 5,077,038), Helioff et al. (U.S. Pat. No. 5,024,779), Remz et al. (U.S. Pat. No. 5,294,435), Miner et al. (U.S. Pat. No. 5,342,536) and Faryniarz et al. (U.S. Pat. No. 5,486,305)).

Solvent systems other than acetone and ethyl acetate have been described in the patent literature for nail lacquer removers, but these have met with limited commercial success. Many of these alternative systems have distinct drawbacks, including health risks and environmental toxicity problems (See, Adams (U.S. Pat. No. 4,543,206), Dotolo et al. (U.S. Pat. No. 5,346,652) and Bayless (U.S. Pat. No. 5,372,742)).

Thickening or gelling systems for enhancing nail polish lacquer removers have also been suggested (See, Minton et al. (U.S. Pat. No. 4,197,212), Day (U.S. Pat. No. 4,804,486) and Miner (U.S. Pat. No. 5,543,085)).

Acetone and methyl acetate (but not ethyl acetate) are currently considered by the California Air Resource Board (CARB) to be low reactivity volatile organic solvents (LR-VOCs) and are EPA-"unlisted" solvents, i.e., their use is largely unrestricted. However, in concentrated form, they are undesirable for many reasons including their unpleasant smell, their excessive volatility and their rapid drying (necessitating application of relatively large quantities of solvent using absorbent cotton balls). Also, their vapors are irritating to the eyes, and they cause desiccation and irritation of the cuticle and skin around the nail. Acetone is also known to cause bronchial irritation and skin erythema via topical exposure. An essentially odor-free liquid nail polish remover having a substantially reduced volatility, based upon the organic solvent gamma butyrolactone is described in Perlman (U.S. Pat. No. 6,521,572).

With the exception of a few LR-VOC solvents such as methyl acetate and acetone that have received exemptions, newly implemented governmental regulations in California require that VOC solvents used in nail polish removers must meet the definition of LVP-VOC solvents, defined as having either a very low vapor pressure (less than 0.1 mm Hg at 20° C.) or a very high boiling point (greater than 216° C.). Unfortunately, most if not all LVP-VOC solvents that are sufficiently active to be useful in nail polish remover formulations, e.g., the alkylene carbonates, are between three and ten times more expensive per pound than acetone. Gamma butyrolactone has neither a sufficiently low vapor pressure nor a sufficiently high boiling point to qualify as an LVP-VOC.

Propylene carbonate-containing nail polish removers and paint strippers have been described previously. Monteleone et al. (U.S. Pat. No. 5,258,070) describe a nail lacquer remover requiring the combination of propylene carbonate, propylene glycol and dimethyl isosorbide. Murase (U.S. Pat. No. 4,801,331) describes a nail lacquer removing composition containing 30%-65% of a carbonate solvent such as propylene carbonate, 10%-50% 1,3-dimethyl-2-imidazolidinone (DMI), 0.2%-20% hydroxypropyl cellulose (thickener) and 13%-40% water. Faryniarz et al. (U.S. Pat. No. 5,486,305) describe a nail polish lacquer remover containing 60%-80% volatile organic solvent (acetone, ethyl acetate and combinations thereof), 3%-20% of a low vapor pressure alkyl or phenyldiester solvent and 5%-20% water. The formulations of Faryniarz et al. may optionally include propylene carbonate (0%-20%), a humectant (0%-20%) and an emollient (0%-10%). In a series of patents, Marquis et al. (U.S. Pat. Nos. 6,040,284, 6,169,061, 6,369,009 and 6,586,380) describe a paint remover containing an alkylene carbonate such as propylene carbonate whose efficacy is enhanced by adding hydrogen peroxide, a strong oxidant. Doscher (U.S. Pat. No. 5,007,969) describes a low toxicity aprotic liquid used for cleaning and for fingernail enamel removal that includes both ethylene diacetate and an alicyclic carbonate solvent that includes propylene and/or ethylene carbonate. Coonan (U.S. Pat. No. 4,594,111) describes a general purpose cleaner-solvent that contains, among other ingredients, from about 50% to about 90% water, from about 5% to about 40% propylene carbonate plus other organic solvents including isopropyl alcohol, diethanolamine (coconut amide) and a tall oil fatty acid. This composition is described as maintaining a pH of 7 and, thus, being non-irritating to normal skin.

BRIEF SUMMARY OF THE INVENTION

This invention concerns a method of improving the chemical stability and increasing the efficacy of alkylene carbonate-containing nail polish removers and also general cleaning products, such as paint removers or strippers. The method includes combining between 10% and 98% by weight of at least one alkylene carbonate solvent, from 1.5% to 25% by weight water and an effective amount of a pH-buffering agent that maintains the pH of the remover composition between approximately pH 2 and pH 6.5. Preferably, the remover composition is provided in a container with a reusable applicator for a liquid or gel composition. The reusable applicator allows the remover to be applied conservatively and not wasted, thereby assuring cost-effective use of the alkylene carbonate-containing composition, which is approximately three times more costly than an acetone-based remover.

Thus, in a first aspect, the present invention relates to nail lacquer removal, and particularly to a method of improving the chemical stability while increasing the efficacy of an alkylene carbonate-containing nail polish remover composition. The method includes combining: (i) between 10% and 98% by weight of at least one alkylene carbonate solvent, (ii) from 1.5% to 25% by weight water, and (iii) an effective amount of a chemically inert pH-buffering agent that maintains the pH of the composition between approximately pH 2 and pH 6.5, preferably between approximately pH 2.5 and 6.0 and, most preferably, between approximately pH 3.0 and pH 5.0 or around pH 4.0. The water functions to increase the rate at which the composition dissolves nail lacquers, and the pH-buffering agent functions to stabilize the alkylene carbonate solvent against hydrolytic decomposition from pH-altering contaminants that may be introduced into the composition.

In one embodiment, the above method includes using between 10% and 25% by weight of at least one alkylene carbonate solvent. In another embodiment, the method includes using between 26% and 50% by weight of at least one alkylene carbonate solvent.

In still another embodiment, the method includes using between 51% and 98% by weight of at least one alkylene carbonate solvent. The use of alkylene carbonate components in an amount greater than 85 wt. %, and preferably between 85 and 90 wt. %, is preferred.

In a preferred embodiment, the alkylene carbonate solvent is selected from the group consisting of propylene carbonate, ethylene carbonate and combinations thereof.

In a related aspect, the method includes adding to the composition a thickener that is soluble and chemically stable, and that can increase the viscosity of the composition to a value of between 100 and 10,000 cps at room temperature.

In a preferred embodiment, the thickener is selected from the group consisting of hydroxypropyl ethylcellulose, hydroxypropyl cellulose, polyoxyethylene oxide, microparticulate fumed silica and combinations thereof.

In another preferred embodiment, the pH-buffering agent is selected from the group consisting of citric acid/citrate buffer, citric acid/dibasic phosphate buffer, acetic acid/acetate buffer, succinic acid/succinate buffer and combinations thereof.

In another related aspect, the method further includes adding to the composition an effective amount of a preservative agent that prevents microbial growth in the composition from introduced contaminants.

In a preferred embodiment, the preservative agent is selected from the group including methylparaben, propylparaben, DMDM hydantoin, ethylenediaminetetracetate and combinations thereof.

In another related aspect, the method further includes adding to the composition up to 20% by weight of at least one glycol, which can serve as a co-solvent to increase the solubility of the water or thicker in the alkylene carbonate solvent, particularly when the composition is subjected to low temperatures. A glycol component in the composition can also serve as a nail and skin humectant.

In preferred embodiments of these aspects of the invention, the glycol is selected from the group consisting of propylene glycol, dipropylene glycol, methylpropanediol glycol and combinations thereof.

In another related aspect, the method further includes adding up to 50% by weight of a low reactivity volatile organic compound (LR-VOC) that complies with governmental regulations for nail polish removers and that is a potent solvent for dissolving nail lacquers.

In a preferred embodiment, the LR-VOC is selected from the group consisting of acetone, methyl acetate and combinations thereof.

In another related aspect, the method further includes adding up to 0.5% by weight of glycerol, which can prevent whitening of the nail surface by the LR-VOC.

In another related aspect, the method employs using a nail polish remover composition that complies with governmental regulations relating to low vapor pressure volatile organic compounds (LVP-VOCs) in nail polish removers.

In a related embodiment, the method employs a composition that, in addition to an alkylene carbonate solvent, includes at least one additional LVP-VOC solvent selected from the group consisting of 2-pyrrolidone, tetraethyleneglycol dimethyl ether, dimethyl adipate and tripropylene glycol methyl ether. These solvents are commonly also known as, respectively, 2-pyrrol, tetraglyme, LVP-dibasic esters (or LVP-DBE) and TPM.

In another related aspect, the method includes packaging the composition in a container, preferably with a reusable applicator.

In a preferred embodiment, the container has a liquid capacity of between one-eighth and eight ounces.

In another preferred embodiment, the reusable applicator is selected from the group consisting of a removable applicator that can be manipulated separately from the container and a permanent or integral applicator that is used as a portion of the container.

In a related embodiment, the removable applicator is selected from the group consisting of a brush, a swab, a spatula and a roller or other rotating device.

In another related embodiment, the permanent applicator is selected from the group consisting of a nib, a brush, a comblike device, an absorbent porous pad, a substantially nonabsorbent porous pad, a porous membrane and a roller or other rotating device. The composition can also be used with disposable applicators, such as cotton balls, foam pads, tissues or sponges.

In another aspect, this invention features a nail polish remover composition that includes between 10% and 98% by weight of at least one alkylene carbonate solvent, from 1.5% to 25% by weight water, which functions to increase the rate at which the composition dissolves nail lacquers, and an effective amount of a pH-buffering agent that is chemically inert in the composition and functions to maintain the pH of the composition between approximately pH 2 and pH 6.5, thereby stabilizing the alkylene carbonate solvent against hydrolytic decomposition from pH-altering contaminants that may be introduced into the composition. Preferably, the pH-buffering agent maintains the pH of the composition between approximately pH 2.5 and pH 6.0 and, most preferably, between approximately pH 3.0 and pH 5.0 or around pH 4.0.

In a related aspect, the composition may further include a thickener that is soluble and chemically stable in the composition and that can increase the viscosity of the composition to a value of between 100 and 10,000 cps at room temperature.

In a preferred embodiment, the alkylene carbonate solvent is selected from the group consisting of propylene carbonate, ethylene carbonate and combinations thereof.

In another preferred embodiment, the pH-buffering agent is selected from the group consisting of citric acid/citrate buffer, citric acid/dibasic phosphate buffer, acetic acid/acetate buffer, succinic acid/succinate buffer and combinations thereof.

In a related aspect, the composition further includes at least one additional LVP-VOC solvent selected from the group consisting of 2-pyrrolidone, tetraethyleneglycol dimethyl ether, dimethyl adipate and tripropylene glycol methyl ether.

In another related aspect, the composition further includes up to 20% by weight of at least one glycol that can serve as a co-solvent to increase the solubility of water in the solvent, and can serve as a nail and skin humectant.

In a preferred embodiment, the glycol is selected from the group consisting of propylene glycol, dipropylene glycol, methylpropanediol glycol and combinations thereof.

In another related aspect, the composition further includes up to 50% by weight of a low reactivity volatile organic compound (LR-VOC) that complies with governmental regulations for nail polish removers and that is a potent solvent for dissolving nail lacquers.

In a preferred embodiment, the LR-VOC is selected from the group consisting of acetone, methyl acetate and combinations thereof.

DESCRIPTION OF THE PREFERRED EMBODIMENT

In the course of testing the efficacy of a wide variety of LVP-VOC solvents as candidates for use in nail polish remover compositions, an unanticipated problem associated with the stability of the composition and the use of a reusable applicator was recognized. It was found that with both propylene carbonate and mixed propylene/ethylene carbonate-containing compositions, their efficacy (speed of dissolving the nail lacquer) was dramatically increased by the addition of water. However, the chemical stability of the aqueous alkylene carbonate removers then became an issue. With the introduction of a reusable applicator that conserved on solvent use, the applicator was observed to have the unforeseen property of carrying contaminants from the nails and fingers back into the reservoir of remover. Some of these contaminants included bacteria and molds as well as alkaline residues from hand soap. It was discovered that the remover stability could be substantially improved by the addition of a pH-buffer and also, preferably, an antimicrobial preservative. According to a preferred embodiment of the present invention, an alkylene carbonate-based nail polish remover in a liquid or gel composition (in which propylene carbonate and/or ethylene carbonate constitute at least 50% by weight of the remover composition) is packaged in a container assembly that includes a reusable applicator device. The applicator may be configured and arranged as either a removable element in the assembly, or it may be configured and arranged as a permanent dispensing applicator portion of the assembly.

As distinguished from the alkylene carbonate-containing paint and nail polish remover compositions of Marquis et al., Monteleone et al., Murase, Faryniarz et al. and Doscher that respectively contain dimethyl isosorbide, 1,3-dimethyl-2-imidazolidinone, dibasic ester solvents, ethylene diacetate, acetone, (m)ethyl acetate and hydrogen peroxide, the composition of the invention does not require these supplemental solvents and oxidants, and it is fortified with an aqueous pH buffer. Thus, in the composition of the invention, the water component accelerates the rate of dissolving of the nail lacquers while the buffer component serves to maintain the pH of the remover composition between approximately pH 2 and 6.5, preferably between approximately pH 2.5 and pH 6.0 and most preferably, between approximately pH 3.0 and pH 5.0 or around pH 4.0, thereby maintaining its resistance to hydrolytic decomposition. That is, paradoxically, if buffer were not added, the same beneficial water could produce a loss in the efficacy, i.e., potency, of the remover due to gradual hydrolysis of ethylene or propylene carbonate to ethylene glycol or propylene glycol, respectively, and carbon dioxide. This potential problem of inadvertently altered pH would not be apparent in a remover consisting of a mixture of propylene or ethylene carbonate plus a more potent nail polish removing solvent such as acetone, in which the alkylene carbonate may be added as a minor constituent of and contributor to the lacquer-dissolving activity of the remover. Nor would the problem be apparent in typical non-aqueous or aprotic organic solvent environments. However, in the present invention, with water being an essential ingredient, and where propylene carbonate is preferably selected to be the principal organic solvent, a breakdown and loss of propylene carbonate would be evident and would destroy the efficacy of the remover. It has also been determined that weak and strong bases, as well as strong acids, accelerate the hydrolysis of these alkyl carbonates. In fact, for maintaining optimal product shelflife, it is important that the pH of liquids containing alkyl carbonate be maintained between pH 2 and pH 6.5 for stability against hydrolytic decomposition. The use of a pH buffer, preferably in the vicinity of pH 4 as described herein, improves the quality of alkylene carbonate-containing products, particularly those products also containing water and/or other protic solvents, and particularly those products that during their utilization and lifetime are susceptible to experiencing pH changes if a pH buffer is not present in the product.

Adding a pH buffer to some alkylene carbonate-containing nail polish remover compositions may be considered optional if the composition is aprotic or free of water and/or there is no opportunity for the reservoir of liquid (or gel) to be chemically or microbially contaminated, and thereby experience a significant change in pH. However, the composition of the present invention always includes an aqueous component and is pH adjusted to the desired range. The means of applying the remover typically involves repeated transfer of the composition from a container to the fingernails, in which a reusable applicator makes repeatedly contact with the composition and the fingernails (or toenails). Among other possible means of contaminating and altering the pH of the composition, the reusable applicator allows inadvertent transfer of residues from the nails back into the reservoir that contains alkylene carbonate remover. These residues may include hand soap that is highly alkaline and may increase the pH of the remover to a range in which the alkylene carbonate decomposes. However, by adding a suitable buffer selected to stabilize the pH between 2 and 6.5 (preferably approximately pH 4), the remover composition can resist changes in pH from inadvertent contaminants.

One of the preferred applications for the pH-buffered alkylene carbonate-based formulations of the present invention is to provide a new brush-on or a fingernail dip-treatment nail polish remover that can replace gamma butyrolactone (GBL)-based formulations. The need for this alternative stems from new environmental regulations that require the elimination of volatile organic compounds (including GBL) that do not meet the definition of LVP-VOCs and LR-VOCs.

However, a problem associated with the use of brush-on nail polish removers is the following. With repeated insertion of the brush into a bottle of nail polish remover liquid, and repeated contact with the fingernails, residues of handsoap and skin creams that may be present on the nails and cuticles tends to be mobilized. Some or all of these residues are then transferred back into the bottle. Handsoap residues tend to be highly alkaline and, thereby, elevate the pH of the nail polish remover liquid. As described above, a shift to alkaline pH will accelerate the hydrolytic decomposition of an alkylene carbonate. Accordingly, the composition of the invention preferably is stabilized as a brush-on nail polish remover by the inclusion of a pH buffer that maintains a slightly acidic pH, i.e., between pH 2 and pH 6.5. This buffer helps neutralize any traces of alkaline soap and also serves to protect the formulation against any other unforeseen pH change. The addition of one or more antimicrobial agents is also advisable, considering that bacterial and fungal species may be introduced into the composition by an applicator that is repeatedly inserted into the container holding the composition.

The utility of the pH-buffering agent in the present invention is also evident even before use. For example, alkylene carbonate-based nail polish removers could be packaged in sealed bottles and in sealed pen-like dispensers, both of which are leak-proof and lack any pressure release valve. If an alkylene carbonate solvent were to begin hydrolyzing due to an increase in pH, e.g., to above pH 7, carbon dioxide would be released within the container, and the bottle or pen could swell under pressure and begin to leak. Here again, the presence of a buffer can help maintain the pH in the mild acidic range and prevent damage to the product.

Either a weak acid, e.g., citric acid, to adjust the pH downward, or a pH-buffering agent (e.g., citric acid plus sodium citrate) can be added to aqueous alkyl carbonate solutions to maintain their hydrolytic stability in a nail polish remover according to the invention. The buffer must be non-reactive with the other constituents in the formulation and otherwise chemically stable over the lifetime of the product. The remover compositions are typically non-toxic and may be biodegraded by microbiological contaminants that may inadvertently be introduced by the consumer into a container of the remover. Therefore, it is also desirable that a preservative (preferably non-toxic) such as disodium EDTA (ethylenediamine tetraacetic acid) be included to prevent solvent breakdown from such accidental contaminants.

As described in the Examples herein, the increase in efficacy, i.e., speed in dissolving hardened lacquer, using a nail lacquer remover according to the invention with an alkylene carbonate solvent supplemented with between 5% and 15% by weight of an aqueous buffer was as great as two-fold. For example, when 8% by weight of 7.5 millimolar citrate buffer pH 4.0 (containing 5 mM citric acid+2.5 mM sodium citrate) was added to propylene carbonate solvent, nitrocellulose-based dried nail lacquer coatings could be dissolved in as little 5-6 seconds by rubbing with a solvent-saturated cotton Q-tip. This was as little as one-half of the 12-13 second time required for propylene carbonate alone (without water) to dissolve identical nail lacquer coatings. This surprising increase in the efficacy of propylene carbonate by addition of aqueous buffer solution was measured to be greater than that increase achieved by adding dimethyl isosorbide and propylene glycol as described by Monteleone et al. (U.S. Pat. No. 5,258,070).

While a nail or skin care cream or treatment liquid would preferably be formulated at neutral pH, and while Coonan (U.S. Pat. No. 4,594,111) teaches a cleaning composition containing propylene carbonate that is maintained at pH 7 to be non-irritating to the skin, this pH is not suited for extended stability of the propylene carbonate. As pointed out above, the product may lose potency, carbon dioxide gas may be released from propylene carbonate hydrolysis and the container may swell or leak. Alkaline as well as strongly acidic conditions can accelerate the decomposition of propylene carbonate and, to even a greater extent, ethylene carbonate. Therefore, the danger in formulating, for example, an aqueous propylene carbonate solution with improved lacquer removing efficacy (faster action) is that the product will also have poor shelf-life. However, at a mildly acidic pH as in the composition according to the invention, the stability and shelf-life of aqueous propylene carbonate can be improved. Thus, as explained above, with the addition of a suitable pH buffer, such as citric acid plus sodium citrate, a mildly acidic pH can be established and maintained. The pH range for stabilizing aqueous propylene carbonate solutions (and those containing other alkyl carbonates such as ethylene carbonate), for achieving a satisfactory shelf life, is between approximately pH 2 and 6.5, with the pH for greatest stability being around pH 4±1. Other constituents may be added, but a pH buffer that maintains the pH within this range, e.g., the combination of a weak acid and a salt of the weak acid, such as the combination of citric acid and sodium citrate, is useful. As a technical matter, a weak acid alone, e.g., acetic acid or citric acid, could be used to adjust the pH of the composition downward to the stability range, and, provided that most contaminants introduced into the composition would be alkaline or neutral, a weak acid alone could function as a buffer and fall within the definition of "buffer" for the purposes of the present invention.

Polycarboxylic acid-containing buffers such as citric acid/sodium citrate will have the additional beneficial property of chelating divalent metal ions that might otherwise accelerate decomposition of the alkyl carbonates. Similarly, a stronger chelator such as EDTA may be added, and this agent has the added benefit of functioning as a preservative by preventing microbial (bacterial and fungal) growth.

While not wishing to be bound by the theory of solvent activity, it is known that common nail lacquers, such as those based upon nitrocellulose coatings, are rapidly solubilized by acetone, ethyl acetate and N-methylpyrrolidone. It is known that these solvents share a Hansen hydrophilic solubility parameter, $SP_h$ (expressed in CGS units) of approximately 3.5. Since the $SP_h$ of propylene carbonate is significantly lower, i.e., only 2.0, it is quite possible that enhancing the hydrophilic environment of this solvent by adding water as a co-solvent (increasing the overall $SP_h$ value) is critical to improving its efficacy. Expressed differently, by adding water, i.e., pH-buffered water, to a nail polish remover based upon propylene carbonate, the remover may behave more like acetone and ethyl acetate that dissolve nail lacquers very rapidly. Water, when mixed with organic solvents, is reported to have an $SP_h$ value of 8.6. Therefore, an aqueous solution containing 92% by weight propylene carbonate and 8% water (the proportion of water that saturates propylene carbonate) should have an $SP_h$ value of approximately 2.5. To increase the $SP_h$ value further towards 3.5, an additional increase in the solubility of water in propylene carbonate would be needed. This increase can be achieved by adding an effective amount of a co-solvent, i.e., a solvent that is miscible in both propylene carbonate and water. For example, a low volatility glycol, diol or polyol such as propylene glycol (PG), dipropylene glycol (diPG), methylpropane diol (MP diol) or combination blend thereof can be added. The co-solvent preferably should be more hydrophilic than propylene carbonate so that it will act together with water to increase the overall hydrophilic nature (and the $SP_h$ value) of the solvent blend. For environmental regulatory reasons, it is preferable that the co-solvent meet the requirements of a low vapor pressure volatile organic compound (abbreviated LVP-VOC) as defined by Federal and/or California Air Resource Board regulations.

From a governmental regulatory perspective, the invention also concerns the selective use of certain LVP-VOCs either alone or in combination with certain low reactivity volatile organic compounds (abbreviated LR-VOCS), the latter of which may enhance the efficacy of nail polish remover formulations, i.e., reduce the time required to dissolve the nail lacquers. Those solvents meeting the definition of LR-VOCs notably include acetone and methyl acetate, both of which are very potent solvents for nitrocellulose-based nail lacquers. LVP-VOCs and LR-VOCs include various other solvents, co-solvents, humectants, emollients, etc. and these have been exempted from the list of volatile organic compounds (abbreviated VOCs) that will be banned from use in nail polish removers under California regulations commencing in 2004. However, most VOCs that have boiling points below 216° C. and vapor pressures exceeding 0.1 mm of mercury at STP (standard temperature and pressure) will be banned in nail polish removers by the California Air Resources Board (CARB) beginning in 2004. For example, NMP (N-methylpyrrolidone) and GBL (gamma-butyrolactone) are excellent solvents for nail polishes but have boiling points somewhat below 216° C. and will be banned. On the other hand, certain dibasic ester solvents such as dibasic esters, e.g., dimethyladipate, and cyclic carbonates such as ethylene carbonate (EC) and propylene carbonate (PC) that have boiling points above 216° C. (or a vapor pressure less than 0.1 mm Hg at 20° C.) will not be banned because they meet the definition of LVP-VOCs. Regarding LR-VOCs, acetone and methyl acetate (but not ethyl acetate) have also been exempted and, therefore, may continue to be used in nail polish remover formulations. Ethyl acetate is not considered a LR-VOC because its reactivity in the atmosphere and in the presence of sunlight in forming ozone is considered greater than ethane (ethane being the ranking "standard").

While propylene carbonate has been used previously in paint and nail polish remover compositions, its activity has depended upon addition of other chemicals, and its stability has never become an issue.

The above-cited propylene carbonate (and/or other alkylene carbonate)-containing compositions, in contrast to those of the present invention, all lack a pH-adjusting and/or a pH-stabilizing agent, e.g., a pH-buffering agent, and all require the addition of one or more supplementary organic solvents or oxidants that are considered less preferable, because of either their cost, their toxicity, their volatility or their irritancy to the skin or eyes. These supplementary solvents have been added to alkylene carbonate-containing compositions of the prior art for achieving lacquer-removing efficacy. Specifically, Monteleone et al. require that dimethyl isosorbide is added, Murase requires that 1,3-dimethyl-2-imidazolidinone is added, Faryniarz et al. require that a $C_4$-$C_{30}$ diester solvent is added (in addition to acetone or ethyl acetate), Marquis et al. requires the addition of hydrogen peroxide, Doscher requires ethylene diacetate and Coonan requires isopropyl alcohol addition. Also, in contrast to the present invention, while Monteleone, Murase and Faryniarz et al. recommend adding water to their formulations, they fail to recognize that a chemical stability problem meriting attention may result from the addition of water.

Definitions. As used in the above description and the accompanying claims, the following terms shall have the meanings indicated, unless the context otherwise requires:

The term "nail lacquer removal" as used herein, refers to a process that involves applying a liquid or gelled solvent-based composition to the fingernails or toenails that have previously been coated with a nail lacquer. The most common nail lacquers are based upon nitrocellulose resins. Current lacquers are either organic solvent-based or water-based and are generally removed using a variety of solvent formulations, as reviewed above. Once the solvent composition has softened and/or dissolved the nail lacquer, the residue can be wiped away using, for example, a paper tissue or cotton ball.

The term "chemical stability" as used herein refers to the resistance of an alkylene carbonate chemical (liquid, gel or solid) to decomposition or breakdown. For an alkylene carbonate, e.g., propylene carbonate or ethylene carbonate ingredient in a liquid or gelled nail polish remover composition, such decomposition could be caused by chemical hydrolysis ("hydrolytic decomposition") and/or by bio-degradation. Accordingly, chemical stability would be favored by including an agent or agents that reduce or prevent such hydrolysis (hydrolysis meaning the chemical addition of water to the molecule). Hydrolysis can be catalyzed by either an acid or a weak or strong alkali being added to (or contaminating) the composition. As taught herein, chemical stability can be promoted by stabilizing the pH of the composition using a pH-buffer. Preventing potential bio-degradation can be accomplished by adding one or more anti-microbial agents, aka preservatives, that prevent growth of bacteria and fungi. Examples of antimicrobials that are used in cosmetics products include, for example, methylparaben, propylparaben, DMDM hydantoin and combinations thereof. Ethylenediaminetetracetate (EDTA) is used in food products as well as in cosmetic products.

The term "efficacy" as used herein refers to the rate at which the nail polish remover composition dissolves nail lacquers. Adding a certain amount of water to an alkylene carbonate solution increases the speed at which it dissolves dried nail lacquer, and therefore increases its efficacy.

The term "alkylene carbonates" refers to the cyclic esters of carbonic acid, the simplest of which is ethylene carbonate. They tend to be environmentally friendly, biodegradable and are powerful solvents for many resin/paint coatings. Alkylene carbonates have high boiling points, flash points, low vapor pressures and low toxicities. Some of the members of the group include propylene carbonate, ethylene carbonate, butylene carbonate and glycerine carbonate. In the context of effective nail polish remover solvents, propylene carbonate, ethylene carbonate, and to a lesser extent butylene carbonate and mixtures thereof are most effective, and are therefore the preferred alkylene carbonate solvents. Since ethylene carbonate has a melting point above room temperature, if it is to be used in a formulation it is preferably blended with propylene carbonate that is liquid at room temperature.

The term "chemically inert" as used herein, refers to a chemical or a material that will not chemically react with the other chemicals in an alkylene carbonate-containing nail polish remover composition. Reversible hydrogen ion transfer in a buffer system is not considered a chemical reaction.

The term "pH-buffering agent" refers to an agent that is chemically inert and is present in a sufficient quantity (sufficient concentration) to hold the original pH of the composition relatively constant, i.e., allowing the pH to change not more than 2.5 pH units, and preferably not more than one pH unit during normal use of the nail polish remover. Normal use could include the repeated use of an applicator to withdraw portions of the remover composition from a container, and apply the composition to the nails. A partial group of examples of suitable pH-buffering agents includes a citric acid/citrate buffer, citric acid/dibasic phosphate buffer, acetic acid/acetate buffer, succinic acid/succinate buffer and combinations thereof. For the pH 2-6.5 range, a weak acid and a salt thereof are typically used to constitute such buffers. Although a broad range of buffer concentrations (measured by molarity) is suitable for use in the present invention, a range of between 1 millimolar and 100 millimolar could be considered useful. A buffer concentration range of between 5 and 25 millimolar would be more commonly considered useful. As pointed out elsewhere, as a technical matter a weak acid alone, e.g., citric acid, could be used to adjust the pH of the composition downward to the stability range, and, provided that most contaminants introduced into the composition would be alkaline (e.g., soap) or neutral, a weak acid alone could function as a buffer and fall within the definition of "pH-buffering agent" for the purposes of the present invention.

As explained herein, water is an essential component of the composition because it increases the rate at which the composition dissolves nail lacquers, while the pH-buffering agent is also essential because it functions to stabilize the alkylene carbonate solvent against hydrolytic decomposition in this aqueous environment (when pH-altering contaminants are introduced into the composition).

The percentage ranges as used herein, e.g., "between 10% and 25% by weight of at least one alkylene carbonate solvent" are defined as including standard rounded up and rounded down numbers. Accordingly, between 10% and 25% is meant to include from 9.50% to 25.49% The term "thickener" herein refers to an agent that is chemically stable, i.e., non-reactive in the solvent-based composition, and that can increase the viscosity of the composition to a value of between 100 and 10,000 centipoise (cps) as measured at room temperature. It is preferable but not required that the thickener is a polymer-based material that remains soluble in the composition and provides a substantially clear or translucent thickened liquid or gel. Thickeners that are commercially available include methylcellulose, hydroxypropyl cellulose, hydroxypropyl ethylcellulose, polyoxyethylene, microparticulate fumed silica and combinations thereof.

The term "preservative agent" is meant to indicate one or more chemical agents that either singly or together, when provided in the remover composition at commercially recommended levels and within any governmental mandated usage limits, prevent microbial growth in the composition. Microbes may be introduced into the composition via a reusable applicator device that is typically and repeatedly used to carry the composition from its storage container to the nails. Some examples of suitable preservative agents that can prevent both bacterial and fungal growth include methylparaben, propylparaben, DMDM hydantoin, ethylenediaminetetracetate and combinations thereof.

The term "co-solvent" is used in the context of being added to the remover composition to increase the solubility of water in the organic solvent (particularly the alkylene carbonate) and/or added to the remover to increase the solubility of a thickener in the organic solvent, particularly when said composition is subjected to low temperatures. In this regard, a number of glycols that are soluble in both water and in alkylene carbonates and that qualify as LVP-VOCs under government regulations for use in nail polish removers are useful. In particular, propylene glycol, dipropylene glycol, methylpropanediol glycol and combinations thereof have been tested, and these have provided the added benefit of serving as a nail and skin humectant. When the alkylene carbonate-containing remover compositions are subjected to low temperatures, e.g., 0° C. to –15° C., there is a tendency for the water component to separate from the organic phase, and the glycol co-solvents help prevent this separation. Glycerol (1,2,3 propanetriol) has been added in small amounts (0.1%-0.5% by weight) to alkylene carbonate-containing remover compositions, not as a co-solvent, but as an effective humectant that prevents undesirable nail streaking and whitening if acetone or methyl acetate is added to the composition. The latter solvents (that comply with governmental regulations for nail polish removers as LR-VOCs) add potency by accelerating the dissolution of lacquers but have a particularly desiccating effect on the surface of the nail that is offset by small amounts of glycerol.

The term "reusable applicator" as used herein refers to any of a wide variety of devices and materials whose function is to transfer the nail polish remover from its storage container and apply it to the lacquer-coated nail surface. The applicator should perform this function efficiently, wasting as little of the remover composition as possible. The requirement for efficiency distinguishes this applicator from the traditional cotton ball that is wasteful in absorbing an excess amount of liquid. Two types of reusable applicators are described, one type being removable and therefore manipulated apart from the container, e.g., a brush, a swab (made, e.g., from a foam or fiber material), a spatula, or a roller or other rotating device, and the other type being an applicator that is a permanent or integral portion of the storage container and is, therefore, used together with the container. The permanent applicator may be in the form of a nib (like a microporous marking pen nib fabricated from polyester or nylon fiber) or other device placed at one end of the container, which allows liquid to slowly flow through the applicator to the surface of the nail. Other functional liquid-permeable devices including a nylon brush, a flexible comb-like device that can distribute fluid over a surface, an absorbent or a substantially non-absorbent porous pad, a porous membrane, or a roller or other rotating device are alternative permanent applicators.

The following examples are presented to illustrate the advantages of the present invention and to assist one of ordinary skill in making and using the same. These examples are not intended in any way otherwise to limit the scope of the disclosure.

EXAMPLE I

Propylene Carbonate-Based Nail Polish Remover Composition

The following constituents were combined in liquid solution at the following percentages by weight:

| | |
|---|---|
| Propylene carbonate | 85.3% |
| Dipropylene glycol | 3.8% |
| Methyl propanediol glycol | 3.0% |
| Aqueous buffer | 7.5% |
| Glycerol | 0.2% |
| Methylparaben | 0.1% |
| Propylparaben | 0.1% |

The above aqueous buffer (pH 4.0) contained 5 mM citric acid, 2.5 mM sodium citrate and 1 mM disodium EDTA. It was constituted as follows: Added to 1000 gm water were: 0.96 gm anhydrous citric acid, 0.73 gm sodium citrate dihydrate, and 0.37 gm disodium ethylenediaminetetraacetate (EDTA) dihydrate.

The above composition was tested and judged to be an effective nail polish remover for dissolving conventional nitrocellulose resin-based nail polishes. Effectiveness was judged as follows. Conventional nitrocellulose nail lacquers were applied as multiple individual fingernail-sized swatches (about 1.5 cm$^2$) on a clean glass plate and fully dried overnight in a 50° C. warming oven. Subsequently, at room temperature, a cotton swab (Q-tip) saturated with the above composition was placed against a dried lacquer swatch and rubbed back and forth (approximately two cycles per second) until the lacquer was fully removed as viewed against a white background. The time interval between initial contact of the swab with the dried lacquer and the complete removal of lacquer was measured by stopwatch. The measured times with repeated trials ranged from four to six seconds. By comparison, Cutex brand "Quick and Gentle®" (Medtech Products, Inc., Jackson, Wyo.) acetone-based remover required only three to four seconds.

EXAMPLE II

Ethylene Carbonate-Propylene Carbonate Blended Nail Polish Remover Composition

The following constituents were combined in liquid solution at the following percentages by weight:

| | |
|---|---|
| Propylene carbonate | 42.7% |
| Ethylene carbonate | 42.6% |
| Dipropylene glycol | 3.8% |
| Methyl propanediol glycol | 3.0% |
| Aqueous buffer | 7.5% |
| Glycerol | 0.2% |
| Methylparaben | 0.1% |
| Propylparaben | 0.1% |

The above composition was tested (same method), compared with that described in Example I and judged to be just as effective a nail polish remover for dissolving conventional nitrocellulose resin-based nail polishes. One possible advantage of including ethylene carbonate is that it increases the capacity of the formulation to dissolve more of the aqueous buffer. Water (in the buffer) increases the rate at which an alkylene carbonate dissolves nail lacquer. For example, 14% by weight buffer, rather than 7.5%, was dissolved in a similar formulation (including both prophylene and ethylene carbonates) without problem. By contrast, the propylene carbonate-based composition in Example I will not accommodate that amount of water. On the other hand, ethylene carbonate is less preferred than propylene carbonate for the following reasons: ethylene carbonate is a solid at room temperature, and its use in such blends with propylene carbonate and water (liquid at room temperature) allows such blends to freeze more easily during shipping in cold climates. Furthermore, while propylene carbonate will break down, if accidentally swallowed, into propylene glycol (non-toxic) and carbon dioxide, ethylene carbonate breaks down to produce ethylene glycol (toxic) and carbon dioxide.

EXAMPLE III

Propylene Carbonate-Based Nail Polish Remover Composition Provided in Containers with Permanently Attached Reusable Applicators Portions of the composition described in Example I were transferred into two pen-like devices, each with a permanently attached reusable applicator. The bodies and some other portions of the devices were fabricated from high density polyethylene and contained manually actuated push-valves that prevented solvent flow except when the applicator end of the device was pressed down against a firm surface. Each device held less than one ounce liquid. One of the devices had a chisel-shaped porous nylon fiber nib as its applicator, and the other device had an essentially flat dacron pad covered with 1.5 mm long fiber tufts that provided scrubbing action to help remove nail lacquer as it was softened by the solvent composition. Both devices functioned without a problem, and the pH of the nail polish remover composition remaining in the devices after exhaustive use was not altered by repeated contact with fingernails and fingers. Moreover, alkaline hand soap residues (pH 11-12) deliberately left on the fingernails and fingers did not alter the pH of the remover composition (pH 4.0) remaining within either of the devices.

EXAMPLE IV

Thickened Propylene Carbonate-Based Nail Polish Remover Composition Provided in a Container with a Removable, Reusable Applicator The composition described in Example I was modified by addition of both a thickener and an LR-VOC solvent in the form of either acetone or methyl acetate as follows: 70 parts by weight of the remover composition in Example I were combined with 30 parts by weight of either acetone or methyl acetate. These acetone or methyl acetate blended compositions were then thickened by adding the soluble polymer, hydroxypropyl methylcellulose (Methocel™ OS manufactured by Dow Chemical Company, Midland Mich.) to a final concentration of approximately 0.5% by weight, and stirring until fully dissolved. This thickener allowed the composition (provided in a one ounce bottle with a nylon brush applicator as part of the removable screw cap closure) to cling to the brush applicator for improved spreading onto the surface of the nail. The addition of an LR-VOC solvent significantly decreased the time required for the thickened compositions to remove dried nail lacquer under the standard test conditions (see Example I). Thus, for example, when the remover composition in Example I was thickened with 0.5% by weight Methocel™ OS, approximately 10-12 seconds was required in the standard test for nail lacquer removal rather than 4-6 seconds for the non-thickened composition. This increased time reflects the reduced solvent activity in a thickened formulation. When the same concentration of Methocel™ OS thickener was added, together with 30% by weight of either acetone or methyl acetate, the lacquer removal time decreased to approximately 4-5 seconds (approximately twice as fast as the same thickened composition without acetone or methyl acetate).

The citric acid plus sodium citrate buffer (7.5 mM concentration) maintained constant pH in the thickened remover composition provided in a bottle, regardless of the number of times that the applicator brush was dipped into the bottle to transfer aliquots of the composition and apply them to fingernails that had been washed with alkaline hand soap. This test was necessary to assure that the composition would not turn alkaline, because alkylene carbonate solvents will decompose to their respective glycols plus carbon dioxide under mildly alkaline conditions and would lose their efficacy.

All patents and publications mentioned in the specification are indicative of the levels of skill of those skilled in the art to which the invention pertains. One skilled in the art would readily appreciate that the present invention is well adapted to carry out the objects and obtain the ends and advantages mentioned, as well as those inherent therein. The specific methods and compositions described herein as representative of preferred embodiments are exemplary and are not intended as limitations on the scope of the invention. Changes therein and other uses will occur to those skilled in the art which are encompassed within the spirit of the invention are defined by the scope of the claims.

It will be readily apparent to one skilled in the art that various substitutions and modifications may be made to the invention disclosed herein without departing from the scope and spirit of the invention. For example, those skilled in the art will recognize that the invention may suitably be practiced using any of a variety of methods and devices to apply the alkylene carbonate removers described herein, and any of a variety of the modifications to the described compositions.

In addition, where features or aspects of the invention are described in terms of Markush groups or other grouping of alternatives, those skilled in the art will recognize that the invention is also thereby described in terms of any individual member or subgroup of members of the Markush group or other group. For example, if there are alternatives A, B and C, all of the following possibilities are included: A separately, B separately, C separately, A and B, A and C, B and C, and A and B and C. Thus, the embodiments expressly include any subset or subgroup of those alternatives, for example, any subset of the types of thickeners, buffers, preservatives and glycols described herein. While each such subset or subgroup could be listed separately, for the sake of brevity, such a listing is replaced by the present description.

The invention illustratively described herein suitably may be practiced in the absence of any element or elements, limitation or limitations which is not specifically disclosed herein. Thus, for example, in each instance herein any of the terms "comprising," "consisting essentially of" and "consisting of" may be replaced with either of the other two terms. The terms and expressions which have been employed are used as terms of description and not of limitation, and there is not an intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims. It is therefore intended that the protection granted by Letters Patent hereon be limited only by the definitions contained in the appended claims and equivalents thereof.

What is claimed is:

1. A nail polish remover composition comprising:
    between 85% and 98% by weight of propylene carbonate solvent;
    between 1.5% and 15% by weight water; and
    an effective amount of a pH-buffering agent that is chemically inert in said composition and that maintains the pH of said composition between approximately pH 2.0 and pH 6.0,
    wherein said composition is free of peroxide, and any organic co-solvent present is a low vapor pressure volatile organic compound (LVP-VOC) or a low reactivity volatile organic compound (LR-VOC).

2. The nail polish remover composition of claim 1, consisting essentially of said propylene carbonate solvent, said water, and said pH-buffering agent.

3. The nail polish remover composition of claim 1, consisting essentially of said propylene carbonate solvent, said water, said pH-buffering agent, a glycol, and optionally a preservative agent that prevents microbial growth in said composition.

4. The nail polish remover composition of claim 1, consisting essentially of said propylene carbonate solvent, said water, said pH-buffering agent, a thickener that is soluble and chemically stable in said composition, and optionally a preservative agent that prevents microbial growth in said composition.

5. The nail polish remover composition of claim 1, consisting essentially of said propylene carbonate solvent, said water, said pH-buffering agent, a glycol, a thickener that is soluble and chemically stable in said composition, and optionally a preservative agent that prevents microbial growth in said composition.

6. The nail polish remover composition of claim 1, wherein any organic co-solvent present is a LVP-VOC.

7. The composition of claim 1, wherein said composition comprises between 85% and 90% by weight of said propylene carbonate solvent.

8. The composition of claim 1, further comprising a thickener that is soluble and chemically stable in said composition, and that can increase the viscosity of said composition to a value of between 100 and 10,000 cps at room temperature.

9. The composition of claim 8, wherein said thickener is selected from the group consisting of hydroxypropyl ethylcellulose, hydroxypropyl cellulose, polyoxyethylene, microparticulate fumed silica and combinations thereof.

10. The composition of claim 1, wherein said pH-buffering agent maintains the pH of said composition between approximately pH 3.0 and pH 5.0.

11. The composition of claim 1, wherein said pH-buffering agent maintains the pH of said composition at about pH 4.0.

12. The composition of claim 1, wherein said pH-buffering agent is selected from the group consisting of citric acid/citrate buffer, citric acid/dibasic phosphate buffer, acetic acid/acetate buffer, succinic acid/succinate buffer and combinations thereof.

13. The composition of claim 1, further comprising an effective amount of a preservative agent that prevents microbial growth in said composition.

14. The composition of claim 13, wherein said preservative agent is selected from the group consisting of methylparaben, propylparaben, DMDM hydantoin, ethylenediaminetetracetate and combinations thereof.

15. The composition of claim 1, further comprising up to 20% by weight of at least one glycol to increase the solubility of said thickener or said water or both in said propylene carbonate solvent.

16. The composition of claim 15, wherein said glycol is selected from the group consisting of propylene glycol, dipropylene glycol, methylpropanediol glycol and combinations thereof.

17. The composition of claim 1, wherein said composition is packaged in a container with a reusable applicator.

18. The composition of claim 17, wherein said container has a liquid capacity of between one-eighth and eight ounces.

19. The composition of claim 17, wherein said reusable applicator is a removable applicator.

20. The composition of claim 19, wherein said removable applicator is selected from the group consisting of a brush, a swab, a spatula, and a roller or other rotating device.

21. The composition of claim 17, wherein said reusable applicator is a permanent applicator that is used as a portion of said container.

22. The composition of claim 21, wherein said permanent applicator is selected from the group consisting of a nib, a brush, a comb-like device, an absorbent porous pad, a substantially non-absorbent porous pad, a porous membrane, and a roller or other rotating device.

23. The composition of claim 1, wherein said composition is free of oxidants.

* * * * *